(12) United States Patent
Gerlach (10) Patent No.: US 12,220,310 B2
(45) Date of Patent: Feb. 11, 2025

(54) OPHTHALMO-SURGICAL INJECTOR

(71) Applicant: Carl Zeiss Meditec AG, Jena (DE)

(72) Inventor: Mario Gerlach, Glienicke-Nordbahn (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 18/115,262

(22) Filed: Feb. 28, 2023

(65) Prior Publication Data

US 2023/0200978 A1 Jun. 29, 2023

Related U.S. Application Data (63) Continuation of application No. PCT/EP2021/072638, filed on Aug. 13, 2021.

(30) Foreign Application Priority Data

Aug. 28, 2020 (DE) ...................... 10 2020 122 597.0

(51) Int. Cl.
*A61F 2/16* (2006.01)

(52) U.S. Cl.
CPC .................................. *A61F 2/1672* (2013.01)

(58) Field of Classification Search
CPC ........ A61F 2/1672; A61F 2/1662–1678; A61F 2/148; A61F 9/0008; A61F 9/007
See application file for complete search history.

(56) References Cited

U.S. PATENT DOCUMENTS

2003/0040755 A1* 2/2003 Meyer ..................... A61F 2/167
606/107

2006/0229634 A1* 10/2006 Shepherd .............. A61F 2/1667
606/107

(Continued)

FOREIGN PATENT DOCUMENTS

| CN | 1520790 A | 8/2004 |
|---|---|---|
| CN | 211271615 U | 8/2020 |

(Continued)

OTHER PUBLICATIONS

Written Opinion of the International Searching Authority dated Dec. 3, 2021 in international application PCT/EP2021/072638, (on which this application is based), and English Language Translation thereof.

(Continued)

*Primary Examiner* — Brigid K Byrd
(74) *Attorney, Agent, or Firm* — Ewers IP Law PLLC; Falk Ewers (57) ABSTRACT

An ophthalmo-surgical injector includes an injector body, a tip with which an intraocular lens can be pressed out of the injector, a first plunger mounted longitudinally displaceably on the injector body and having a first projection, a shaft rotatably mounted in the injector body and having a first guide and a second guide which are each wound about the shaft, and a second plunger mounted longitudinally displaceably on the injector body and having a second projection. The first projection engages in the first guide, such that the first plunger is configured to effect, with a longitudinal displacement of the first plunger, a rotation of the shaft about a longitudinal axis of the injector body, and the second projection engages in the second guide, as a result of which the shaft is configured to effect, with the rotation effected by the first plunger, a longitudinal displacement of the second plunger.

11 Claims, 4 Drawing Sheets

(56) References Cited

U.S. PATENT DOCUMENTS

| | | | |
|---|---|---|---|
| 2010/0160926 A1 | 6/2010 | Artsyukhovich et al. | |
| 2016/0135994 A1* | 5/2016 | Romoda ............. | A61F 9/00781 606/108 |
| 2017/0172798 A1* | 6/2017 | Horvath ............. | A61M 5/3286 |

FOREIGN PATENT DOCUMENTS

| | | |
|---|---|---|
| JP | 2014050484 A | 3/2014 |
| WO | 2020151908 A1 | 7/2020 |

OTHER PUBLICATIONS

Office Action issued in parallel Chinese Patent Application No. 202180053122.5, dated Sep. 28, 2023, and English language translation thereof.

Office Action issued in German Patent Application No. DE 10 2020 122 597.0, dated Jun. 11, 2021 (from which this application claims priority) and English machine translation thereof.

International Search Report dated Dec. 3, 2021 of international application PCT/EP2021/072638 on which this application is based, and English translation thereof.

\* cited by examiner

OPHTHALMO-SURGICAL INJECTOR

CROSS REFERENCE TO RELATED APPLICATIONS

This application is a continuation application of international patent application PCT/EP2021/072638, filed Aug. 13, 2021, designating the United States and claiming priority to German application 10 2020 122 597.0, filed Aug. 28, 2020, and the entire content of both applications is incorporated herein by reference.

TECHNICAL FIELD

The disclosure relates to an ophthalmosurgical injector for inserting an intraocular lens into the capsular bag of an eye.

BACKGROUND

In cataract treatment of an eye, only a small incision is usually made in the cornea of the eye, said incision being large enough to allow a tip of an injector to be inserted into the eye through the incision. After the incision has been made in the cornea, the lens of the eye is usually broken up by phacoemulsification and then sucked out of the capsular bag of the eye. Thereafter, an intraocular lens is inserted into the eye with the injector. In the process, a plunger of the injector displaces the intraocular lens within the injector and out of the injector. While the intraocular lens is being displaced, the intraocular lens is folded such that it fits through the tip of the injector and the incision in the cornea. The tip is inserted into the capsular bag through the incision in the cornea, and the folded intraocular lens is pushed through the tip into the capsular bag with the injector, whereupon the intraocular lens unfolds in the capsular bag and thus replaces the original lens.

Figure 4:
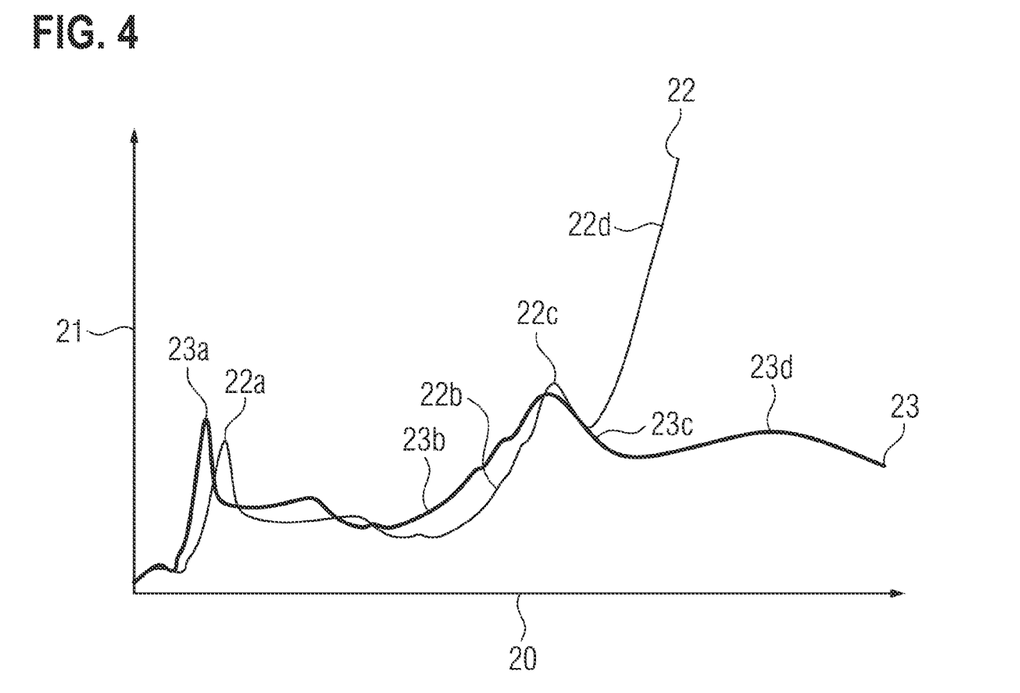
FIG. 4 shows a force-displacement curve for a conventional injector and for the injector according to an exemplary embodiment of the disclosure, respectively.

During the displacement of the intraocular lens through different portions of the injector, resistance forces of different magnitudes occur. FIG. 4 illustrates an example of a force-displacement curve 22 of a plunger of a conventional injector, wherein the displacement path 20 of the plunger is plotted along the horizontal axis and the force 21 applied during the displacement is plotted along the vertical axis. It is apparent that very different forces have to be applied along the displacement path of the injector. The local maximum of the force with the reference sign 22a results from the plunger being released from a safety lock. The increase in the force in the region identified by the reference sign 22b results from the fact that the intraocular lens is pushed from a storage chamber into a folding chamber which narrows in the direction of the tip and in which the intraocular lens is folded and elastically deformed. The drop in the force in the region identified by the reference sign 22c can be explained by the fact that the intraocular lens is pushed from the folding chamber into the tip, wherein the tip narrows at a flatter angle in the direction of the outlet of the tip than the folding chamber. The particularly steep increase in the force in the region of the reference sign 22d results from the fact that the intraocular lens and a plunger tip of the plunger are compressed at the end of the tip. The strong force can collapse abruptly when the intraocular lens leaves the injector, and this can have the result that the intraocular lens passes into the capsular bag at high speed and therefore in an uncontrolled manner.

WO 2020/151908 A1 describes an injector for injecting an intraocular lens, wherein the injector has a speed regulator. US 2010/0160926 A1 describes a device for injecting an intraocular lens and techniques for compensating for variations in the resistance during injection. US 2006/0229634 A1 describes an apparatus and a method for inserting an intraocular lens into an eye.

SUMMARY

It is therefore an object of the disclosure to improve a force-displacement curve that occurs when an intraocular lens is displaced in an injector.

The ophthalmosurgical injector according to an aspect of the disclosure has an injector body, a tip with which an intraocular lens can be pushed out of the injector, a first plunger which is mounted on the injector body so as to be longitudinally displaceable and has a first protrusion, a shaft which is mounted rotatably in the injector body and has a first guide slot and a second guide slot which each wind around the shaft, and a second plunger which is mounted on the injector body so as to be longitudinally displaceable and has a second protrusion, wherein the first protrusion engages in the first guide slot, with the result that the first plunger is configured to bring about a rotation of the shaft about a longitudinal axis of the injector body as a result of a longitudinal displacement of the first plunger, and the second protrusion engages in the second guide slot, with the result that the shaft is configured to bring about a longitudinal displacement of the second plunger as a result of the rotation brought about with the first plunger.

With the shaft, a transmission ratio is created between the longitudinal displacement of the first plunger and the longitudinal displacement of the second plunger. With the pitch of the first guide slot and the pitch of the second guide slot, a value of the transmission ratio can be set. The transmission ratio can be defined for example as the ratio of a force applied to the second plunger to a force applied to the first plunger. Since the transmission ratio is set, it is possible to improve a force-displacement curve of a force which is to be applied during the longitudinal displacement of the first plunger. For example, it is conceivable to select the transmission ratio such that a larger force is applied to the second plunger than to the first plunger. As a result, a lower force needs to be exerted on the first plunger by an operator than if the transmission ratio were not provided. The pitch of the first guide slot and the pitch of the second guide slot may be defined for example as the inclination of the respective guide slot with respect to the circumferential direction of the shaft. In order that the first guide slot and the second guide slot wind and thus the longitudinal displacement of the first plunger results in the rotation of the shaft and the rotation of the shaft results in the longitudinal displacement of the second plunger, the pitches of the first guide slot and of the second guide slot are other than zero and infinite.

It is also conceivable for the transmission ratio to vary during the longitudinal displacement of the first plunger and of the second plunger. As a result, a force-displacement curve can be altered during the longitudinal displacement of the first plunger and of the second plunger such that it is flatter, with the result that the force-displacement curve is likewise improved. For example, it is conceivable to select a high transmission ratio in regions of the longitudinal displacement of the second plunger in which a high force needs to be overcome and to select a low transmission ratio in regions of the longitudinal displacement of the second plunger in which a weak force needs to be overcome. In order that the transmission ratio varies, it is conceivable for the pitch of at least one of the two guide slots to vary during the longitudinal displacement, wherein it is also conceivable for the pitches of both guide slots to vary during the longitudinal displacement.

It is typical for the injector to be configured to convert the longitudinal displacement of the first plunger toward the tip into the longitudinal displacement of the second plunger toward the tip. The second plunger is typically configured, as a result of its longitudinal displacement, to push the intraocular lens into the tip and subsequently to push it out of the injector. In addition, it is typical for the longitudinal displacement of the first plunger and of the second plunger to take place in a direction that is substantially parallel to the axial direction of the shaft.

A pitch ratio of the pitch of the first guide slot at the position in which the first protrusion engages to the pitch of the second guide slot at the position in which the second protrusion engages varies typically during the longitudinal displacement of the first plunger and of the second plunger. The pitch of the first guide slot and the pitch of the second guide slot may be defined for example as the inclination of the respective guide slot with respect to the circumferential direction of the shaft. A larger pitch is thus associated with a shorter rotation of the shaft per unit of longitudinal displacement. By this definition, the pitch ratio is identical to the transmission ratio and to a force ratio of a force acting on the second plunger in the axial direction of the shaft to a force acting on the first plunger in the axial direction of the shaft.

It is typical for the pitch ratio to become larger at least in some portions during the longitudinal displacement of the first plunger and of the second plunger toward the tip. As a result, it is possible to flatten an increase in the force-displacement curve caused by the intraocular lens being folded and/or elastically deformed. The pitch ratio increases particularly typically monotonically along an end region of a displacement path of the second plunger toward the tip. In the end region of the displacement path of the second plunger, the intraocular lens and a plunger tip of the second plunger are compressed particularly greatly, resulting in a particularly large rise in the force-displacement curve. Therefore, it is particularly relevant to flatten the force-displacement curve in this region. It is also conceivable for the pitch ratio to increase strictly monotonically. It is additionally particularly typical for the pitch ratio to be larger than one along an end region of a displacement path of the second plunger toward the tip. As a result, the force to be applied to the first plunger by the operator can be reduced. Because the force that is to be applied in order to displace the intraocular lens longitudinally in this region is particularly high, it is particularly advantageous to reduce the force to be applied by the operator in this region. In addition, it is thus possible to avoid a situation in which the intraocular lens leaves the injector at high speed and thus in an uncontrolled manner. For example, the pitch ratio at the end of the force-displacement curve may be larger than 3.0 and in particular larger than 4.0.

It is typical for the pitch ratio to be larger than one along a starting region of a displacement path of the second plunger toward the tip. As a result, it is possible for example to flatten an increase in the force-displacement curve caused by a safety lock being released by the first plunger.

The first guide slot typically has a first portion and a second portion which each wind around the shaft, and a portion oriented in the axial direction of the shaft, via which portion the first protrusion can pass from the first portion into the second portion as a result of its longitudinal displacement away from the tip. As a result, it is necessary to press the first plunger twice in order that the first protrusion travels along the entire first guide slot. As a result, a particularly high transmission ratio can be achieved. It is also conceivable for more than two of the portions that wind around the shaft to be provided and, for in each case two adjacent ones of the winding portions, in each case one portion that is oriented in the axial direction of the shaft to be provided, via which portion the first protrusion can pass from one of the adjacent winding portions into the other of the adjacent winding portions as a result of its longitudinal displacement away from the tip. It is particularly typical for the injector to have a preloading means which is configured to preload the first plunger in a direction away from the tip. As a result, the first protrusion passes automatically from the first portion into the second portion as soon as the protrusion is arranged at the end of the first portion and the force is removed from the first plunger. The preloading means may be for example a compression spring.

It is typical for the injector to have a stop which is configured to limit a movement of the shaft toward the tip.

The injector typically has a first anti-rotation means which is configured to prevent rotation of the first plunger relative to the injector body. Alternatively or additionally, the injector typically has a second anti-rotation means which is configured to prevent rotation of the second plunger relative to the injector body. As a result, it is possible to prevent the first plunger and/or the second plunger from being set in rotation during their longitudinal displacement.

It is typical for the shaft to be a hollow shaft and thus to have a cavity, wherein the first plunger is arranged at least partially and at least temporarily in the cavity during its longitudinal displacement and/or wherein the second plunger is arranged at least partially and at least temporarily in the cavity during its longitudinal displacement. As a result, the injector can be embodied in a particularly space-saving manner.

It is typical for the shaft to be a hollow shaft and thus to have a cavity, wherein the first guide slot and/or the second guide slot extend, in a radial direction of the shaft, all the way through a wall, bounding the cavity, of the shaft. Alternatively, it is conceivable for the first guide slot and/or the second guide slot each to be in the form of a groove in the case of the hollow shaft.

Alternatively, it is typical for the shaft to be embodied without a cavity in its interior and for the first guide slot to be in the form of a groove and/or for the second guide slot to be in the form of a groove.

The injector typically has the intraocular lens. The intraocular lens is typically arranged in the injector body. In particular, at the start of the longitudinal displacement of the first plunger, wherein the first plunger is as far as possible away from the tip at the start, the intraocular lens may be arranged in a storage chamber of the injector, wherein the storage chamber is arranged on a side of the folding chamber facing away from the tip.

BRIEF DESCRIPTION OF THE DRAWINGS

The disclosure will now be described with reference to the drawings wherein.

DESCRIPTION OF EXEMPLARY EMBODIMENTS

Figure 1:
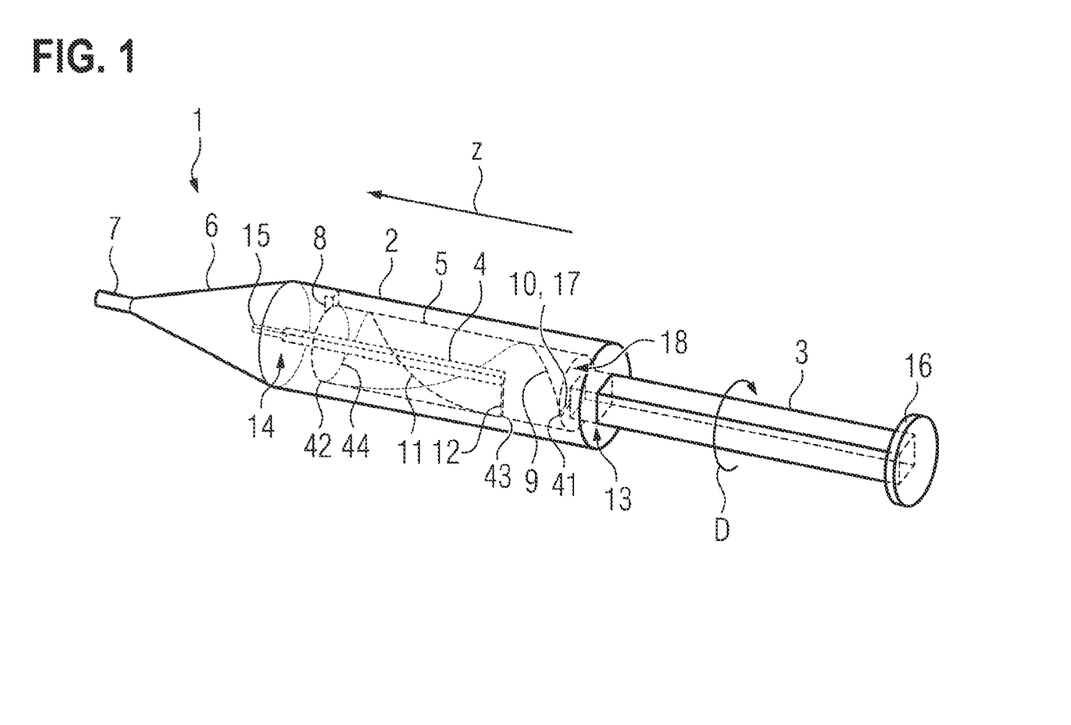
FIG. 1 shows an injector at a first time according to an exemplary embodiment of the disclosure.
Figure 2:
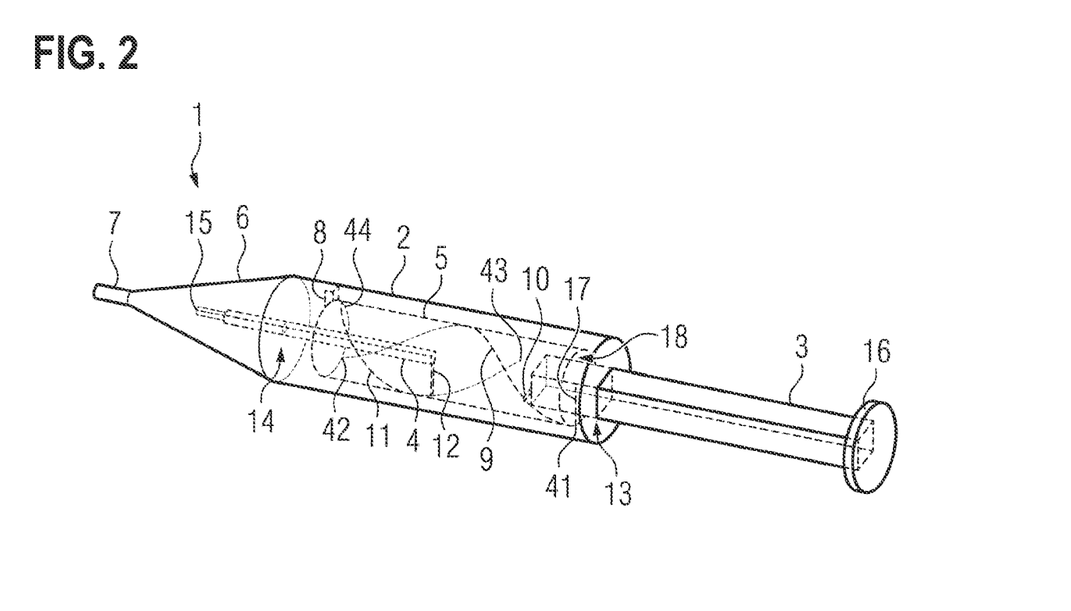
FIG. 2 shows the injector at a second time.
Figure 3:
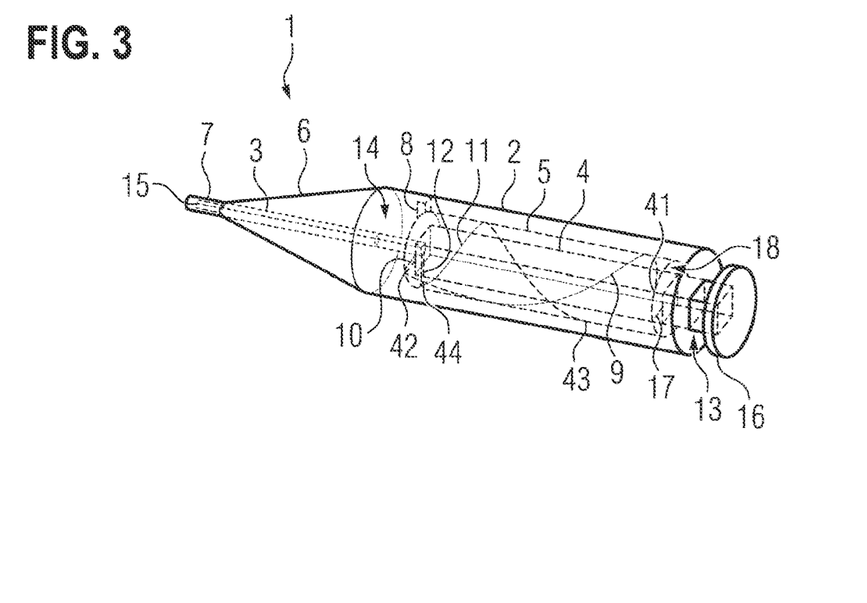
FIG. 3 shows the injector at a third time.

As is apparent from FIGS. 1 to 3, an ophthalmosurgical injector 1 has an injector body 2, a tip 7 with which an intraocular lens 1 can be pushed out of the injector 1, a first plunger 3 which is mounted on the injector body 2 so as to be longitudinally displaceable and has a first protrusion 10, a shaft 5 which is mounted rotatably in the injector body 2 and has a first guide slot 9 and a second guide slot 11 which each wind around the shaft 5, and a second plunger 4 which is mounted on the injector body 2 so as to be longitudinally displaceable and has a second protrusion 12. The first protrusion 10 engages in the first guide slot 9, with the result that the first plunger 3 is configured to bring about a rotation of the shaft 5 about a longitudinal axis of the injector body 2 as a result of a longitudinal displacement or movement in translation of the first plunger 3. The second protrusion 12 engages in the second guide slot 11, with the result that the shaft 5 is configured to bring about a longitudinal displacement or movement in translation of the second plunger 4 typically along the longitudinal axis of the injector body 2 as a result of the rotation of the shaft 5 brought about with the first plunger 3.

In order that the first guide slot 9 and the second guide slot 11 wind and thus the longitudinal displacement of the first plunger 3 results in the rotation of the shaft 5 and the rotation of the shaft 5 results in the longitudinal displacement of the second plunger, the first guide slot 9 and the second guide slot 11 can have pitches which are other than zero and infinite. The pitch of the first guide slot 9 and the pitch of the second guide slot 11 may be defined for example as the inclination of the respective guide slot 9, 11 with respect to the circumferential direction D of the shaft 5. If the respective guide slot 9, 11 had an infinite pitch in one region, this would correspond to an orientation of the region only in the axial direction z of the shaft 5. If the respective guide slot 9, 11 had a pitch of zero in one region, this would correspond to an orientation of the region only in the circumferential direction D of the shaft 5.

FIG. 1 shows the injector 1 at a first time at which the first plunger 3 is as far away from the tip 7 as possible. FIG. 3 shows the injector 1 at a third time at which the first plunger 2 is arranged as close to the tip 7 as possible. FIG. 2 shows the injector 1 at a second time which lies temporally between the first time and the third time and at which the first plunger 3 is arranged in a position between the position of the first plunger 3 at the first time and the position of the first plunger 3 at the third time. FIGS. 1 to 3 show that the injector 1 can be configured to convert the longitudinal displacement of the first plunger 3 toward the tip 7 into the longitudinal displacement of the second plunger 4 toward the tip 7, wherein the longitudinal displacement of the first plunger 3 and of the second plunger 4 take place substantially in the axial direction z of the shaft 5. It is apparent from the shape of the first guide slot 9 that, when the first plunger 3 is displaced toward the tip 7, the shaft 5, as seen in a direction from the first plunger 3 to the tip 7, is set in rotation in a counterclockwise direction. It is apparent from the shape of the second guide slot 11 that the rotation of the shaft 5 in the counterclockwise direction results in the second plunger 4 being displaced toward the tip 7. The rotation in the counterclockwise direction is likewise apparent from the pointer 17 which is drawn on the end side of the shaft 5 facing away from the tip 7.

In order to allow the first protrusion 10 to move in the first guide slot 9 and the second protrusion 12 to move in the second guide slot 11 with as little friction as possible, the contacting surfaces of the guide slots 9, 11 and of the protrusions 10, 12 may have been provided with a surface treatment, the injector 1 may have a lubricant which is configured to act between the contacting surfaces of the guide slots 9, 11 and of the protrusions 10, 12 and/or the injector 1 may have a respective ball bearing for each of the two guide slots 9, 11, wherein a respective ball of the ball bearing has been incorporated into each of the protrusions 10, 12.

The second plunger 4 may be configured, as a result of its longitudinal displacement, to push the intraocular lens into the tip 7 and subsequently to push it out of the injector 1. To this end, a plunger tip 15 may be arranged at that end of the second plunger 4 that faces away from the first plunger 3, said plunger tip being formed by a soft cushion or a fork. The longitudinal displacement of the second plunger 4 toward the tip may have the result that, at the end of the longitudinal displacement of the second plunger 4, the second plunger 4 extends all the way through the tip 7. It is also conceivable for the plunger tip 15 to be arranged outside the injector 1 at the end of the longitudinal displacement of the second plunger 4.

The injector 1 may have a storage chamber in which the intraocular lens is intended to be inserted or has already been inserted. In addition, the injector 1 may have a folding chamber 6 in which the intraocular lens is folded and compressed during the longitudinal displacement of the second plunger 4. It is conceivable for the folding chamber 6 to narrow in the direction of the tip 7 for this purpose. It is additionally conceivable for the folding chamber 6 to be arranged between the storage chamber and the tip 7 in the axial direction z of the shaft 5. The tip 7 may narrow in the direction of an outlet of the tip 7, wherein it is conceivable here for the tip 7 to narrow less steeply than the folding chamber 6. In addition, it is conceivable for the injector 1 to have the intraocular lens. In this case, it is conceivable for the intraocular lens to be arranged in the injector body 2 and in particular in the storage chamber. It is also apparent from FIGS. 1 to 3 that the first plunger 3 can have a thumb rest 16 at its longitudinal end facing away from the shaft 5.

FIGS. 1 to 3 show that the injector 1 can have a stop 8 which is configured to limit a movement of the shaft 5 toward the tip 7. In addition, FIGS. 1 to 3 show that the injector 1 can have a first anti-rotation means 13 which is configured to prevent rotation of the first plunger 3 relative to the injector body 2. To this end, in a plane, the normal of which is parallel to the axial direction z of the shaft 5, the first plunger 3 may have a cross section other than a circular cross section, which engages with a form fit in a first opening of the injector body 2. Additionally or alternatively, the injector 1 may have a second anti-rotation means 14 which is configured to prevent rotation of the second plunger 4 relative to the injector body 2. To this end, in a plane, the normal of which is parallel to the axial direction z of the shaft 5, the second plunger 4 may have a cross section other than a circular cross section, which engages with a form fit in a second opening of the injector body 2.

As is apparent from FIGS. 1 to 3, the shaft 5 may be a hollow shaft and thus have a cavity 18, wherein the first plunger 3 is arranged at least partially and at least temporarily in the cavity 18 during its longitudinal displacement and/or wherein the second plunger 4 is arranged at least partially and at least temporarily in the cavity 18 during its longitudinal displacement. Here, the first guide slot 9 and/or the second guide slot 11 can extend, in a radial direction of the shaft 5, all the way through a wall, bounding the cavity 18 of the shaft 5. Alternatively, it is conceivable for the first guide slot 9 to be in the form of a groove and/or for the second guide slot 11 to be in the form of a groove.

Figure 5:
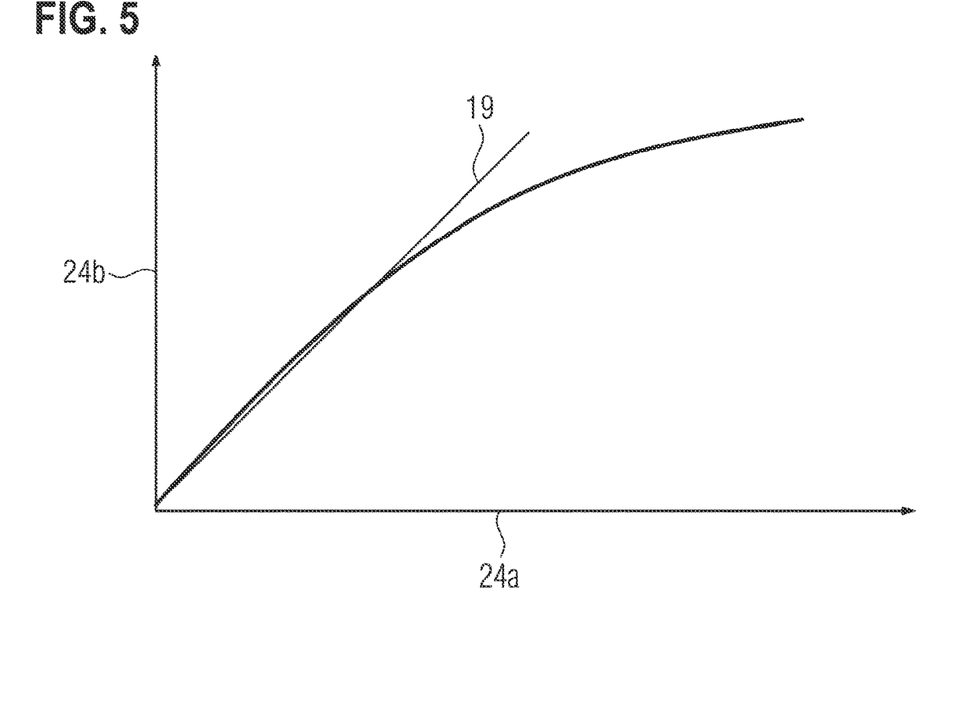
FIG. 5 shows, for a first exemplary embodiment of the injector, the plot of a displacement path of a first plunger of the injector versus a second plunger of the injector.

FIGS. 1 to 3 show that the first guide slot 9 may have a starting point 41 at which the first protrusion 10 is arranged at the first time and an end point 42 at which the first protrusion 10 is arranged at the third time. The distance from the starting point 41 of the first guide slot 9 to the end point 42 of the first guide slot 9 in the axial direction z of the shaft 5 corresponds to the maximum displacement path of the first plunger 3. In addition, the second guide slot 11 may have a starting point 43 at which the second protrusion 12 is arranged at the first time and an end point 44 at which the second protrusion 12 is arranged at the third time. The distance from the starting point 43 of the second guide slot 11 to the end point 44 of the second guide slot 11 in the axial direction z of the shaft 5 corresponds to the maximum displacement path of the second plunger 4. The distance of the starting point 41 of the first guide slot 9 from the end point 42 of the first guide slot 9 in the circumferential direction D of the shaft corresponds to the distance of the first protrusion 10 from the second protrusion 12 in the circumferential direction D of the shaft 5 in a radial spacing of the shaft 5 at which the guide slots 9, 11 are arranged. FIGS. 1 to 3 show that the maximum displacement path of the first plunger 3 can be longer than the maximum displacement path of the second plunger 4. This is illustrated for example in FIG. 5 in a plot in which a displacement path 24a of the first plunger 3 is plotted along the horizontal axis and a displacement path 24b of the second plunger 4 is plotted along the vertical axis. Also plotted is the angle bisector 19. It is apparent that in the case of short displacement paths 24a of the first plunger 3, the second plunger 4 can cover a longer displacement path 24b than the displacement path 24a of the first plunger 3 and that in the case of longer displacement paths 24a of the first plunger 3, the first plunger 3 can cover a longer displacement path 24a than the displacement path 24b of the second plunger 4. Since the first plunger 3 covers a longer displacement path 24a than the displacement path 24b of the second plunger 4, during the longitudinal displacement, a force acting on the first plunger 3 in the axial direction z of the shaft 5 is converted into a stronger force acting on the second plunger 4.

Figure 6:
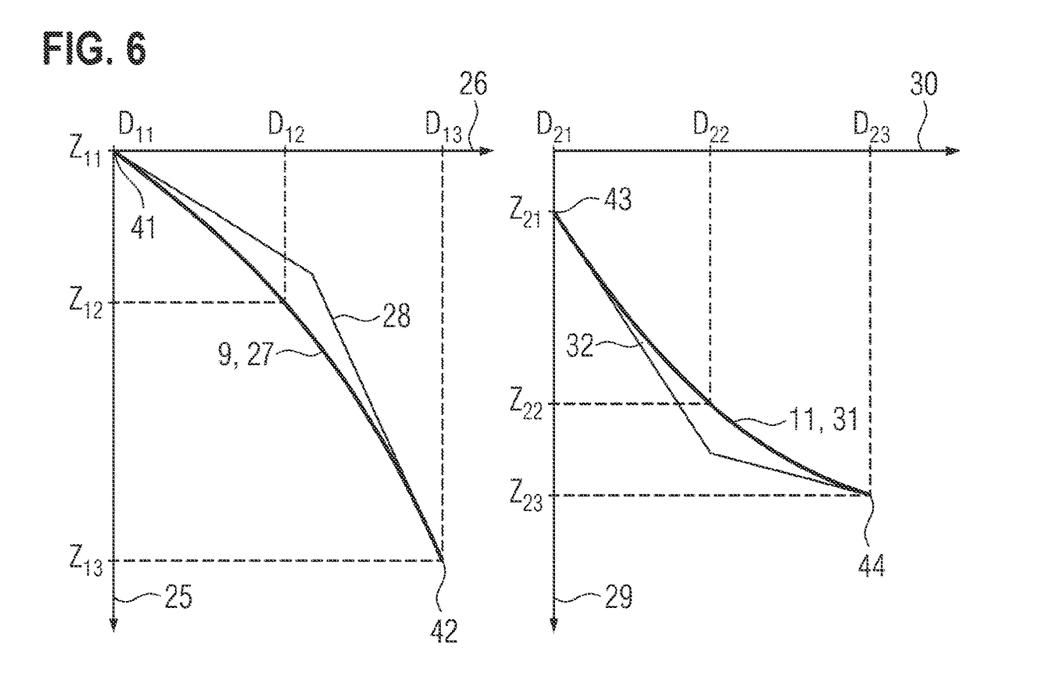
FIG. 6 shows, for the first exemplary embodiment, a shape of a first guide slot and of a second guide slot, respectively.
Figure 7:
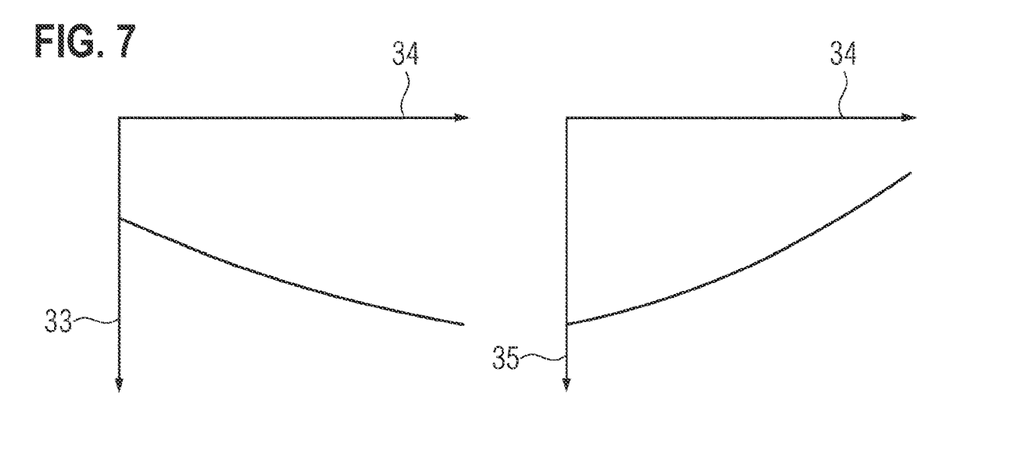
FIG. 7 shows, for the first exemplary embodiment, the pitch of the first guide slot and the pitch of the second guide slot.
Figure 8:
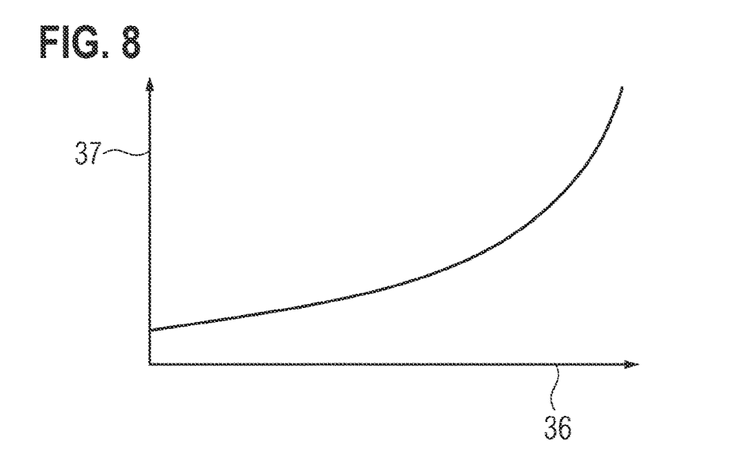
FIG. 8 shows, for the first exemplary embodiment, the plot of a pitch ratio of the pitch of the first guide slot to the pitch of the second guide slot.

FIGS. 6 to 8 illustrate various diagrams of a first exemplary embodiment of the injector 1. In FIG. 6, the shape of the first guide slot 9 is illustrated in the left-hand plot and the shape of the second guide slot 11 is illustrated in the right-hand plot. In the left-hand plot, the distance 26 of the first guide slot 9 from the starting point 41 of the first guide slot 9 in the circumferential direction D of the shaft 5 is plotted along the horizontal axis and the distance 25 of the first guide slot 9 from the starting point 41 of the first guide slot 9 in the axial direction z of the shaft 5 is plotted along the vertical axis. In the right-hand plot, the distance 30 of the second guide slot 11 from a reference point, located on the shaft 5, in the circumferential direction D of the shaft 5 is plotted along the horizontal axis and the distance 29 of the second guide slot 11 from the reference point in the axial direction z of the shaft 5 is plotted along the vertical axis. The plots in FIG. 6 thus correspond to a developed surface of the shaft 5. The shape of the first guide slot 9 may, as illustrated, be a Bezier curve 27, wherein the associated control polygon 28 is drawn in. The shape of the second guide slot 11 may, as illustrated, be a Bezier curve 31, wherein the associated control polygon 32 is drawn in. Instead of the Bezier curves 27, 31, other curve shapes are also conceivable, for example polynomials or splines. In the plots, (D11, z11) are the position of the first protrusion 10 at the first time, (D21, z21) are the position of the second protrusion 12 at the first time, (D12, z12) are the position of the first protrusion 10 at the second time, (D22, z22) are the position of the second protrusion 12 at the second time, (D13, z13) are the position of the first protrusion 10 at the third time, and (D23, z23) are the position of the second protrusion 12 at the third time. Because the distance of the first protrusion 10 from the second protrusion 12 is invariable in the circumferential direction D of the shaft during longitudinal displacement, the following applies: D13−D11=D23−D21 and D12−D11=D22−D21.

In FIG. 7, the pitch 33 of the first guide slot 9 from FIG. 6 is plotted in the left-hand plot and the pitch 35 of the second guide slot 11 from FIG. 6 is plotted in the right-hand plot, in each case with respect to a rotation angle 34 of the shaft 5. In FIG. 8, the pitch ratio 37 of the pitch 33 of the first guide slot 9 from FIG. 7 to the pitch 35 of the second guide slot 11 from FIG. 7 versus a displacement path 36 of the second plunger 4 is illustrated. The pitch ratio 37 is identical to a force ratio of a force acting on the second plunger 4 in an axial direction z of the shaft 5 to a force acting on the first plunger 3 in an axial direction z of the shaft 5. In FIG. 8, the pitch ratio 37 versus the displacement path 36 of the second plunger 4 for a second exemplary embodiment of the injector 1 is plotted, wherein, in the second exemplary embodiment, the shapes of the first guide slot 9 and of the second guide slot 11 are different than the shapes of the first guide slot 9 and of the second guide slot 11 of the first exemplary embodiment.

Figure 9:
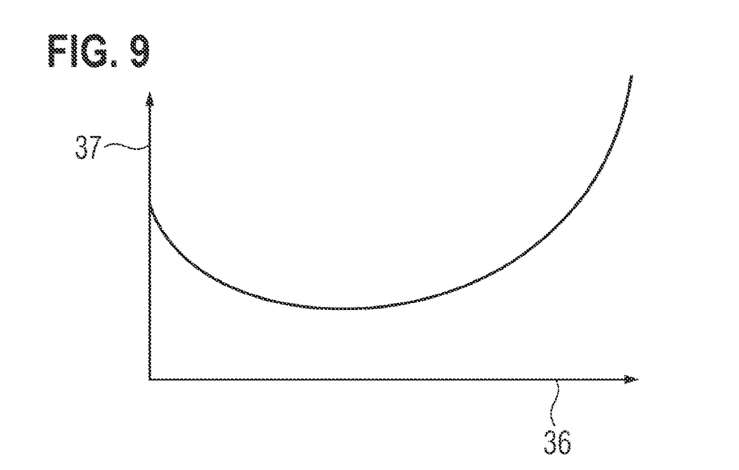
FIG. 9 shows a pitch ratio for a second exemplary embodiment of the injector.

It is apparent from FIGS. 8 and 9 that a pitch ratio 37 of the pitch 33 of the first guide slot 9 at the position in which the first protrusion 10 engages to the pitch 35 of the second guide slot 11 at the position in which the second protrusion 12 engages can vary during the longitudinal displacement of the first plunger 3 and of the second plunger 4. It is also apparent that the pitch ratio 37 can become larger at least in some portions during the longitudinal displacement of the first plunger 3 and of the second plunger 4 toward the tip 7. In both exemplary embodiments, the pitch ratio 37 increases monotonically, and in particular strictly monotonically, along an end region of a displacement path of the second plunger 3 and thus also along an end region of a displacement path 36 of the first plunger 3 toward the tip 7. It is conceivable for the pitch ratio 37 to increase monotonically, and in particular to increase strictly monotonically, along the entire displacement path 36 of the first plunger 3, as is the case for example in the first embodiment. Alternatively, it is conceivable for the pitch ratio 37 to drop monotonically, and in particular to drop strictly monotonically, along a starting region of the displacement path of the second plunger 4 and thus also along a starting region of the displacement path 36 of the first plunger 3 toward the tip 7, as is the case in the second exemplary embodiment.

In particular for the first exemplary embodiment and the second exemplary embodiment, it is conceivable for the pitch ratio 37 to be larger than one or larger than 3.0 or larger than 4.0 along an end region of a displacement path of the second plunger 4 and thus also along an end region of a displacement path 36 of the first plunger 4 toward the tip 7. In particular for the second embodiment, it is conceivable for the pitch ratio 37 to be larger than one along a starting region of a displacement path of the second plunger 4 and thus also along a starting region of a displacement path 36 of the first plunger 3 toward the tip 7. For the second exemplary embodiment, it is additionally conceivable for the pitch ratio 37 to be less than 1 in a region of the displacement path 36 of the first plunger 3 that lies between the starting region and the end region of the first plunger 3. As a result, in regions of the displacement path 36 of the first plunger 3 in which a great deal of force is necessary to displace the intraocular lens, the transmission ratio is selected such that the force acting on the second plunger 4 in the axial direction z is stronger than the force acting on the first plunger 3 in the axial direction z of the shaft 5. At the same time, in regions of the displacement path 36 of the first plunger 3 in which only a little force is necessary to displace the intraocular lens, the transmission ratio is selected such that the force acting on the second plunger 4 in the axial direction z of the shaft 5 is weaker than the force acting on the first plunger 3 in the axial direction z of the shaft 5.

FIG. 4 illustrates a comparison of a force-displacement curve 22 of a conventional injector, which does not have a transmission ratio, with a force-displacement curve 23 of the first plunger 3 of the second exemplary embodiment of the injector 1. The displacement path 20 of the first plunger 3 of the second exemplary embodiment and the displacement path 20 of the plunger of the conventional injector, respectively, are plotted along the horizontal axis, and the force 21 applied for displacement is plotted along the vertical axis. It is apparent that the displacement path 20 of the second exemplary embodiment is much longer and that the increase in the force in the region 23d is much lower than the increase in the force in the region 22d.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS

1 Injector
2 Injector body
3 First plunger
4 Second plunger
5 Shaft
6 Folding chamber
7 Tip
8 Stop
9 First guide slot
10 First protrusion
11 Second guide slot
12 Second protrusion
13 First anti-rotation means
14 Second anti-rotation means
15 Plunger tip
16 Thumb rest
17 Pointer
18 Cavity
19 Angle bisector
20 Displacement path
21 Force
22 Force-displacement curve of a plunger of a conventional injector
23 Force-displacement curve of the first plunger of the injector according to the disclosure
24a Displacement path of the first plunger
24b Displacement path of the second plunger
25 Distance of the first guide slot in the axial direction
26 Distance of the first guide slot in the circumferential direction
27 First Bezier curve
28 First control polygon
29 Distance of the second guide slot in the axial direction z
30 Distance of the second guide slot in the circumferential direction D
31 Second Bezier curve
32 Second control polygon
33 Pitch of the first guide slot
34 Rotation angle of the shaft
35 Pitch of the second guide slot
36 Displacement path of the first plunger
37 Pitch ratio/force ratio
41 Starting point of the first guide slot
42 End point of the first guide slot
43 Starting point of the second guide slot
44 End point of the second guide slot
z Axial direction
D Circumferential direction
$z1x$ Axial position of the first plunger at an x-th time
$D1x$ Circumferential position of the first protrusion relative to the shaft at an x-th time
$z2x$ Axial position of the second plunger at an x-th time
$D2x$ Circumferential position of the second protrusion relative to the shaft at an x-th time

What is claimed is:

1. An ophthalmosurgical injector, comprising:
an injector body;
a tip with which an intraocular lens can be pushed out of the injector;
a first plunger mounted longitudinally displaceably on the injector body and having a first protrusion;
a shaft mounted rotatably in the injector body and having a first guide slot and a second guide slot which each wind around the shaft; and
a second plunger mounted longitudinally displaceably on the injector body and having a second protrusion,
wherein the first protrusion engages in the first guide slot, such that the first plunger is configured to bring about a rotation of the shaft about a longitudinal axis of the injector body as a result of a longitudinal displacement of the first plunger,
wherein the second protrusion engages in the second guide slot, such that the shaft is configured to bring about a longitudinal displacement of the second plunger as a result of the rotation brought about with the first plunger, and
wherein a pitch ratio of a first pitch of the first guide slot at the position in which the first protrusion engages to a second pitch of the second guide slot at the position in which the second protrusion engages is along an entire driving path larger than zero and smaller than infinite, wherein the first pitch defines a first positive inclination of the first guide slot along the entire driving path, and wherein the second pitch defines a second positive inclination of the second guide slot along the entire driving path.

2. The injector as claimed in claim 1, wherein the pitch ratio becomes larger at least in some portions during the longitudinal displacement of the first plunger and of the second plunger toward the tip.

3. The injector as claimed in claim 2, wherein the pitch ratio increases monotonically along an end region of a displacement path of the second plunger toward the tip.

4. The injector as claimed in claim 1, wherein the pitch ratio is larger than one along an end region of a displacement path of the second plunger toward the tip.

5. The injector as claimed in claim 1, wherein the pitch ratio is larger than one along a starting region of a displacement path of the second plunger toward the tip.

6. The injector as claimed in claim 1, wherein the shaft is a hollow shaft and has a cavity, wherein the first plunger is arranged at least partially and at least temporarily in the cavity during the longitudinal displacement of the first plunger, and/or wherein the second plunger is arranged at least partially and at least temporarily in the cavity during the longitudinal displacement of the second plunger.

7. The injector as claimed in claim 1, wherein the shaft is a hollow shaft and has a cavity, and wherein the first guide slot and/or the second guide slot extend, in a radial direction of the shaft, all the way through a wall, bounding the cavity, of the shaft.

8. The injector as claimed in claim 1, wherein the first guide slot is a first groove, and/or wherein the second guide slot is a second groove.

9. The injector as claimed in claim 1, wherein the pitch ratio of the first pitch of the first guide slot at the position in which the first protrusion engages to the second pitch of the second guide slot at the position in which the second protrusion engages varies during the longitudinal displacement of the first plunger and of the second plunger.

10. The injector as claimed in claim 1, wherein the first and second guide slots are arranged on an inner surface of the shaft.

11. The injector as claimed in claim 1, wherein the first pitch is defined as the first positive inclination with respect to a circumferential direction of the shaft from a proximal end of the first guide slot to a distal end of the first guide slot, and wherein the second pitch is defined as the second positive inclination with respect to the circumferential direction of the shaft from a proximal end of the second guide slot to a distal end of the second guide slot.

* * * * *